United States Patent [19]

Sackner

[11] Patent Number: 5,040,540

[45] Date of Patent: Aug. 20, 1991

[54] METHOD AND APPARATUS FOR NON-INVASIVE MONITORING OF CENTRAL VENOUS PRESSURE, AND IMPROVED TRANSDUCER THEREFOR

[75] Inventor: Marvin A. Sackner, Miami Beach, Fla.

[73] Assignee: Nims, Inc., Miami Beach, Fla.

[21] Appl. No.: 510,456

[22] Filed: Apr. 17, 1990

Related U.S. Application Data

[62] Division of Ser. No. 235,672, Aug. 24, 1988, Pat. No. 4,986,277.

[51] Int. Cl.$^5$ .............................................. A61B 5/02
[52] U.S. Cl. .................................... 128/672; 128/693; 128/680; 128/380
[58] Field of Search ............... 128/672, 675, 680, 681, 128/687, 688, 691, 693, , 694, 713, 714, 380, 639, 644, 734, 721, 402

[56] References Cited

U.S. PATENT DOCUMENTS

| 3,349,825 | 10/1967 | Andreadis | 128/402 |
| 4,016,868 | 4/1977 | Allison | 128/644 |
| 4,452,252 | 6/1984 | Sackner | 128/721 |
| 4,648,407 | 3/1987 | Sackner | 128/721 |

FOREIGN PATENT DOCUMENTS 2124704  5/1971  Fed. Rep. of Germany ...... 128/644

Primary Examiner—Stephen C. Pellegrino
Assistant Examiner—Robin R. Longo
Attorney, Agent, or Firm—Schechter, Brucker & Pavane

[57] ABSTRACT

A method and apparatus for measuring central venous pressure (CVP) is disclosed, along with an improved transducer (50) for measuring CVP in infants. Changes in CVP may also be monitored by employing the method and apparatus of the invention.

6 Claims, 8 Drawing Sheets

FIG. 1

$CVP = (h)\ cmH_2O$

FIG. 9 ns METHOD AND APPARATUS FOR NON-INVASIVE MONITORING OF CENTRAL VENOUS PRESSURE, AND IMPROVED TRANSDUCER THEREFOR

This is a divisional of U.S. application Ser. No. 07/235,672, filed Aug. 24, 1988, now U.S. Pat. No. 4,986,277.

BACKGROUND OF THE INVENTION

1. Field of the Invention

This invention pertains to non-invasive monitors, and more particularly to non-invasive monitoring of cardiac function.

2. Prior Art

The prior art teaches transducers placed on the neck for detecting internal jugular and carotid pulse waveforms. See, for example, Tavel, *Clinical Phonocardiography and External Pulse Recording*, Year Book Medical Publishers, Inc., 3d Ed., 1978, pp. 25-32. Transducers placed on the neck have also been used by the present inventor for obtaining carotid pulse waveforms and for monitoring respiratory events, as described in U.S. Pat. No. 4,452,252, which suggests use of a particular transducer, denominated the neck inductive plethysmograph. This patent, at column 6, also suggests placing two such transducers about the neck for obtaining both respiratory and cardiac waveforms, depending upon the type of filtering used.

While the cardiac information derived from such transducers is useful, it is not substitutable for venous pressure measurements. Venous pressure measurements are a widely recognized diagnostic tool for assessing cardiac function. Elevation of venous pressure is common in congestive heart failure and may precede other signs such as peripheral edema, ascites, pleural effusion and liver enlargement. For obvious reasons, venous pressure trends are more valuable than a single value of the absolute venous pressure level.

Measurement of peripheral venous pressures have long been utilized to follow the course of congestive heart failure, but peripheral pressures may be altered by local venoconstriction. Therefore, measurement of venous pressure within the central venous system, i.e. superior vena cava, has become the preferred site of measurement for assessing overall hemodynamic function, and numerous investigations have confirmed the clinical usefulness of central venous pressure (CVP) for hemodynamic monitoring. Further, CVP generally reflects the degree of hypovolemia (low circulating blood volume) thereby providing a guide to fluid replacement therapy.

A review of the invasive and visual methods for determination of peripheral venous pressures is found in Burch, *A Primer of Venous Pressure*, Lea & Febiger, 1950. For both invasive and visual methods, errors due to improper selection of reference level for the influence of gravity need to be considered. In order to overcome such errors, a point in the venous system must be utilized at which the venous pressure is equal to that of the atmosphere. Since none of the points of reference is always at "zero" or atmospheric pressure, it is important to employ a satisfactory standard level of reference which all observers can utilize to obtain comparative values. Burch, supra, selected the phlebostatic axis or "heart level"—defined as the line of junction between (1) a transverse plane of the body passing through the points of junction of the lateral margins of the sternum and the fourth intercostal space of the rib cage and (2) a frontal plane of the body passing through the midpoint of a line extending from the outermost point of the anterior surface of the sternum and the outermost point of the posterior surface of the chest—as a satisfactory reference point for venous pressures.

Many techniques have been advocated for invasively measuring the venous pressure in peripheral veins. Burch, supra. Trends in such pressures generally agree with central venous pressures (CVP) in the high ranges but diverge in the low ranges. In hypovolemia (low circulating blood volume), peripheral venous pressures largely reflect local influences upstream from their site of measurement and inaccurately estimate the degree of hypovolemia. See Shoemaker et al., *Textbook of Critical Care*, W. B. Saunders Company, 1984; Rippe et al., *Intensive Care Medicine*, Little Brown and Company, 1985.

For direct measurement of CVP, invasive, CVP monitoring (continuous measurement of superior vena cava pressure) by insertion of central venous catheters is routinely employed, and CVP derived, from such catheters is used to guide fluid therapy after hemorrhage, accidental and surgical trauma, sepsis, and emergency conditions associated with blood volume deficits. Shoemaker, supra; Rippe, supra.

A healthy ambulatory person in the supine posture may have CVP values up to about 6 cmH$_2$O. Ten to 12 cmH$_2$O is frequently used as the upper limit of normal for acutely ill patients. However, critically ill patients receiving mechanical ventilation and positive end-expiratory pressure (PEEP), who require fluid volume to maintain arterial pressure, may develop CVP values of 20 to 25 cmH$_2$O. Shoemaker, supra; Rippe, supra.

CVP measurements are highly useful during early resuscitation from acute cardiac injury. Increased CVP usually indicates that fluids have been administered too rapidly. CVP is most helpful when there is failure of only one organ system, such as cardiac failure or uncomplicated blood loss. Change in CVP in response to a fluid volume challenge over a prescribed time period reflects the reserve capacity of the heart.

From a simplistic point of view, the CVP level appears to be determined by blood volume and right heart function. Large fluid infusions produce only small changes of CVP in the hypovolemic patient, but increased blood volume elevates CVP in the overtransfused stressed patient. Fluid overload precipitously increases CVP in patients with cardiac disease. However, despite the apparently simple relation between CVP and blood volume, it is inadvisable to rely solely on CVP as a reliable measure of circulating blood volume, as there are several factors which influence CVP values, not the least of which are cardiac performance, blood volume and vascular tone, intrinsic venous tone, increased intra-abdominal or intrathoracic pressures, and vasopressor therapy Shoemaker, supra; Rippe, supra.

Four sites are commonly utilized for insertion of central venous catheters: the antecubital veins, internal or external jugular veins, femoral vein, and subclavian vein. Central catheters have considerable risks, and at least one of the routes carries a significant morbidity rate comparable to that of an appendectomy. The internal jugular, subclavian, and femoral vein approaches should not be used in patients with trauma in the region, local infection, previous thrombosis, or any anatomic anomaly. Although systemic infection is a relative contraindication to central venous catheterization (in general, any invasive instrumentation should be avoided in a septic patient), the patient with septic shock requires rapid fluid and medication administration, and peripheral cannulation may prove impossible thereby necessitating central venous catheterization Shoemaker, supra; Rippe, supra.

To obtain a valid central venous pressure,, the catheter tip should be placed within the right atrium or one of the great veins of the thorax (e.g., the superior vena cava, the innominate vein, or subclavian vein) The most desirable site for the catheter tip is the distal innominate or proximal superior vena cava. The right atrium itself should be avoided since many complications can occur at this site including: (1) perforation of the atrial wall with resultant potentially lethal cardiac tamponade (hemorrhage into the pericardium), (2) irritation of the atrial wall producing arrhythmias, and (3) migration of the catheter tip to the inferior vena cava, hepatic veins, right ventricle, or pulmonary arteries. Shoemaker, supra; Rippe, supra.

There are a variety of complications that may result from central venous catheterization performed through the antecubital veins. These include sterile phlebitis, infection, and deep venous thrombosis (of subclavian or internal jugular veins). Other rare complications included tamponade, puncture of central veins, air embolism, catheter embolism and limb edema.

The most common complication with internal jugular venous (IJV) cannulation is carotid artery puncture, and unrecognized arterial puncture is potentially life threatening. Accordingly, if there is any doubt whether venipuncture or arterial puncture has been performed, catheters should not be threaded over the guide wire. Nonvascular complications also occur from internal jugular venous catheterization. Pneumothorax and hydro- and hemothorax may rarely occur, as may chylothorax when the left IJV. approach is used. Other rare complications include catheter tip migration out of the vasculature, air embolism, erosion of a venous wall and hydrothorax, thrombophlebitis, and pulmonary embolism. Shoemaker, supra; Rippe, supra. While, external jugular venous (EJV) cannulation avoids some of these problems, the success rate of this route is substantially lower than the IJV route.

Three main complications are associated with femoral venous (FV) cannulation: arterial puncture, infection, and thromboembolic events. Inadvertent femoral arterial puncture has been reported in up to six percent of cannulations with most of these occurring in patients with pulseless femoral arteries. Shoemaker, supra; Rippe, supra.

The subclavian venous approach to central venous catheterization has received the greatest attention of all routes used for central venous access. However, the rare occurrence of serious or potentially life-threatening complications renders the technique dangerous in clinical situations where complications are more likely to occur (e.g., prior surgery in the subclavian area), or in patients who cannot tolerate the complication of pneumothorax (e.g., patients with chronic obstructive pulmonary disease or acute respiratory distress syndrome).

The complications reported from subclavian venous catheterization and indwelling catheter placement include malposition of catheter tip, local cellulitis, pneumothorax, pleural effusion, hemo- or hydrothorax, subcutaneous emphysema, hydromediastinum, mediastinal hematoma, suppurative mediastinitis, clavicular osteomyelitis, subclavian artery puncture, brachial plexus injury, myocardial perforation with or without tamponade, phrenic nerve injury with diaphragmatic paralysis, arteriovenous malformations, endotracheal tube cuff rupture, catheter embolism, air embolism, infectious complications, venous thrombosis, innominate or SVC perforation, thoracic duct injury with or without chylothorax, venobronchial fistula, and internal mammary artery injury. Shoemaker, supra; Rippe, supra.

Most reports indicate 0 to 5 episodes of infection per 100 catheters, regardless of the route of insertion or length of time the catheter is in place. This assumes that a standardized protocol is used to insert all central lines, and that maintenance of the catheter (bandage changes) is carried out by an "intravenous team," an important factor in reducing the number of such episodes. The incidence of catheter-associated infections generally increases proportionally with (1) the duration of, the catheter use, (2) number of catheters inserted into the central circulation versus peripheral location, (3) number of catheters placed by surgical cutdown, (4) number of breaks in technique, and (5) number of "unauthorized" manipulations of the catheter. Shoemaker, supra; Rippe, supra.

As the foregoing demonstrates, invasive access to monitoring of CVP carries a high risk of both immediate and late complications. Where such catheters are required solely for monitoring trends in CVP rather than for administration of fluids and drugs, non-invasive monitoring is highly preferred, since complications are nil.

A non-invasive visual method for estimating venous pressure is based upon the clinical observation that in normal erect subjects, the veins of the neck are collapsed and cannot be seen, while in patients with congestive heart failure who have elevated venous pressures, the jugular veins located in the neck are distended by the increased pressure within these veins. It has been stated that the vertical distance from the suprasternal notch to the top of the column of blood visible in the external jugular vein reflects the degree of venous pressure elevated above the normal. Burch, supra.

It should be noted, however, that distention of the internal jugular veins, though less obvious than distention of the external jugular veins, more accurately reflects the central venous pressure, as the internal jugular vein is contiguous with the superior vena cava (the site for central venous pressure), and there are no intervening valves to interrupt blood flow. While visualization of the top of the column of blood in the internal jugular vein would therefore provide a more accurate measure of CVP, the internal jugular is typically visualized only with the aid of specialized lighting, and its visualization is difficult even for highly skilled physicians. In many cases, the internal jugular vein is so deep that its blood column cannot be visualized by even the most skilled physicians. This is particularly the case in obese patients and patients with highly developed neck muscles.

It is therefore an object of the invention to provide a non-invasive method and apparatus for measurement of central venous pressure which is not dependent on visual inspection of the jugular veins.

Intracranial pressure, like central venous pressure, has major diagnostic and managerial significance, particularly in neonatal neurological disorders. For example, intracranial pressure may prove useful in evaluating infants with intraventricular hemorrhage, posthemorrhagic hydrocephalus, hypoxic-ischemic encephalopathy, bacterial meningitis, and a variety of other pathological states, and also for evaluating the effects of certain interventions such as external ventricular drainage or lumbar puncture for treatment of posthemorrhagic hydrocephalus. Intracranial pressure alterations per se may lead to adverse consequences by disturbing cerebral blood flow and, less frequently, by shifting neural structures in the brain. J. Volpe, *Neurology of the Newborn*, 2d Ed., W. B. Saunders Company, 1987.

Since central venous pressure approximates intracranial pressure, monitoring of intracranial pressure also provides information about central venous pressure and, as described above, such information is valuable in the diagnosis and management of a variety of disorders. Salmon et al., *The Fontagram: A Noninvasive Intracranial Pressure Monitor*, Pediatrics, Vol. 60, No. 5, November, 1977. Ordinarily, intracranial venous pressure is coupled to intracranial pressure since, in order for the veins to remain patent, their pressure must be slightly higher than the surrounding pressure. This coupling has been shown to occur over a wide range of pressures when intracranial pressure is altered. Since the cerebral venous pressure cannot be less than the systemic venous pressure, the cerebral venous pressure and the intracranial pressure only become uncoupled when the latter is lowered below the systemic venous pressure. Welch, *The Intracranial Pressure in Infants*, Journal of Neurosurgery, Vol. 52, May, 1980.

Though invasive techniques are available, they are, not suited to continuous monitoring or even frequent intermittent determinations. According, non-invasive techniques are preferred. Known non-invasive monitors rely on the anterior fontanel as an indicator of intracranial pressure. More particularly, these devices rely on the applanation principle, which recognizes that when the anterior fontanel is flat, the pressure on both sides of the fontanel is equal, and therefore that the pressure required to maintain the fontanel flat should equal intracranial pressure. Several devices exploiting the applanation principle have been developed, all of which incorporate means for applying a positive pressure to the anterior fontanel sufficient to flatten it and means for measuring that pressure Volpe, supra, Salamon et al., supra. While some studies have reported good correlation between actual intracranial pressure and intracranial pressure as measured with these devices, it is possible that the pressure required to flatten the fontanel does not match intracranial pressure, as depressing the fontanel may simply bulge other intracranial sites, such as the sutures and the occipital fontanel.

A non-invasive visual approach to measuring intracranial pressure, which also relies on the applanation principle, is disclosed in Welch, supra. With the infant in the dorsal recumbent position, the fontanel is observed and palpated. If it is flat, the vertical distance between the level of the fontanel and the level at which venous pressure is thought to be atmospheric (e.g. the midpoint of the clavicle) is measured, and this height, in centimeters, is said to approximate intracranial pressure in cmH$_2$O. If the fontanel is not flat, the head is raised or lowered until the fontanel becomes flat, whereupon the vertical distance measurement is made. The potential inaccuracies of this visual approach are obvious.

A further difficulty of measuring intracranial pressure in infants is that any transducer applied to the infant, particularly at the head, must be both comfortable and secure, otherwise the infant will continuously attempt to remove the transducer, with obvious adverse consequences to long term monitoring.

It is accordingly another object of the invention to provide a method and apparatus for monitoring intracranial pressure, and also to provide an improved transducer therefor which is specifically intended for use with infants.

SUMMARY OF THE INVENTION

The present invention is based upon the recognition that changes in the dimensions of the neck, as measured by an inductive plethysmographic transducer band or any other transducer suitable for such measurements (See U.S. Pat. Nos. 4,452,252 and 4,456,015, the entire contents of which are incorporated herein by reference), depict pulses synchronous with the heart beat which resemble venous, arterial or a mixture of venous and arterial waveforms, and that the particular waveform depicted may be used as a basis for determining central venous pressure and for monitoring changes therein.

More particularly, in the horizontal or head-down postures; waveforms from such transducers usually depict a venous configuration. This is because distension of the neck veins by blood, as a result of gravity relative to the phlebostatic axis in the horizontal posture, causes large internal jugular venous pulsations which obscure the smaller pulsations from the less compliant neck arteries (about one tenth the compliance of the veins) and from the smaller diameter external jugular veins. However, when the upper portion of the body is elevated by means of a tilt table or with a hospital bed to the semi-recumbent posture, a point is reached at which the waveform changes to a mixed venous-arterial or arterial configuration. It is believed that this occurs because the internal jugular vein walls collapse as a result of gravity when their height exceeds the level of pressure at the phlebostatic level.

The point at which the venous pulse in the neck is replaced by the venous-arterial or arterial pulse waveform defines the pressure of the more distal venous vessel nearer the right atrium of the heart, e.g. the superior vena cava. The present invention comprises measuring the height with respect to the phlebostatic axis at which the waveform level changes from a venous to a venous-arterial or arterial configuration when the neck is raised above the phlebostatic axis. Measurement of this height in centimeters can be construed as the superior vena cava or central venous pressure (CVP) in cmH$_2$O since the specific gravity of blood is near unity. The result is a discrete non-invasive measurement of CVP.

It should be noted that the phlebostatic axis is preferred as the reference level because the pressure at this axis is at or near atmospheric pressure, and accordingly to arrive at CVP no adjustment to the vertical distance measured in accordance with the method of the invention is necessary. However, it is possible to utilize other reference levels not at atmospheric pressure and still arrive at CVP in accordance with the present invention, but this will require adding to or subtracting from the vertical distance measured in accordance with the invention the amount by which the reference pressure varies from atmospheric. For example, if the reference level is two cmH$_2$O above atmospheric, the vertical distance in centimeters as measured in accordance with the invention must be reduced by two centimeters to arrive at the correct CVP in cmH$_2$O. Accordingly, as used herein, the term "reference level" is to be understood as encompassing any appropriate reference level having a known pressure relative to atmospheric such that CVP may be calculated from the vertical distance measured in accordance with the invention, and whenever it is stated that this vertical distance equals or approximates CVP, it also should be understood that this only applies if the reference level is at atmospheric pressure, and that otherwise the vertical distance must be adjusted to reflect the amount by which the reference level varies from atmospheric.

In accordance with another aspect of the present invention, changes in direction of CVP, either upwards or downward, can be continuously monitored if the posture is maintained at the discrete determination point and the waveforms from two vertically spaced neck transducers are monitored. Thus, at the posture for determination of CVP, the waveform from the transducer at the base of the neck closest to the heart shows a venous appearance while the upper transducer depicts a venous-arterial or arterial configuration. If this posture is maintained and the waveform from the upper neck transducer changes to a pure venous configuration, a rise in. CVP is indicated. On the other hand, a change in the waveform from the lower neck transducer to a venous-arterial or arterial configuration indicates a decline in CVP. As described more fully below, trend information also can be obtained with a single transducer, though such information is more limited than that obtainable with dual transducers.

In accordance with another aspect of the present invention, CVP measurements may be made in newborns with open fontanel and sutures using a transducer disposed about the head. As with the neck transducer described above, the upper portion of the infant's body is elevated, as by a tiltable incubator or hospital bed, until the transition point is reached at which the waveform from the transducer changes from a venous configuration to a mixed venous-arterial or arterial configuration. At that point, the height in centimeters from the transducer to the phlebostatic axis provides a good approximation of CVP in cmH$_2$O.

In accordance with yet another aspect of the invention, a novel transducer for placement about the infant's head is disclosed. The novel transducer basically comprises a modified stocking cap of the type placed on the heads of newborns for keeping them warm. The novel transducer comprises a tube of stretchable material closed at one end, with the other end being folded back on itself for defining a hem, with a conductive loop threaded or otherwise secured in the hem, such that when the cap is placed on the infant's head, the conductive loop encircles the head for expansion and contraction with the cap in response to cardiopulmonary events. A primary advantage of the novel transducer is that it may be incorporated in a conventional stocking cap and, as such, is comfortable to wear and requires no separate securement to the infant. This particular transducer is only effective in infants, as the cardiopulmonary events of interest are detectable by the transducer only until the cranial bones fuse, which typically occurs by no later than 18 months.

Further features and advantages of the methods and apparatus of the present invention will be more fully apparent from the following detailed description and annexed drawings of the presently preferred embodiments thereof.

DETAILED DESCRIPTION OF THE PREFERRED EMBODIMENT

Figure 1:
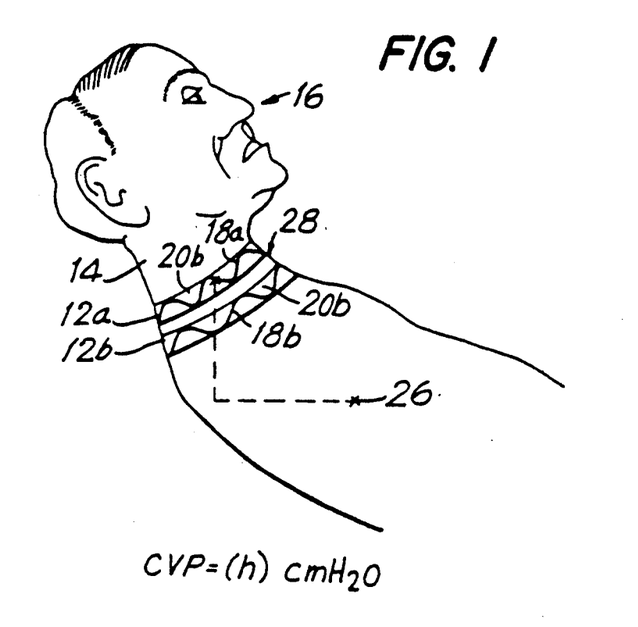
FIG. 1 is a diagrammatic representation of dual transducers for practicing the method of the invention, with the subject shown in a semi-recumbent position.

Referring now to the drawings, and initially to FIG. 1 thereof, a preferred apparatus for practicing the present invention comprises a pair of transducers 12a, 12b disposed in spaced, substantially parallel relation about the neck 14 of a subject 16. Each transducer 12a, 12b preferably comprises a neck inductive plethysmograph (NIP), though, from this description, those of ordinary skill in the art will recognize that other transducers, such as mercury in silastic strain gauges, bellows pneumographs or linear differential transformers, may be employed.

The preferred transducer, the neck inductive plethysmograph, comprises an extensible electrically conductive loop 18 supported on an elastic tube 20 disposed in close encircling relation about the neck 14 of the subject 16. The tube 20 preferably has two free ends (not shown) which may be releasably connected, as by Velcro strips, to facilitate placement about the neck 14. Each conductive loop 18 is rendered extensible by, for example, forming the loop in a shape approximating a sine wave, such that the conductive loop 18 expands and contracts with expansions and contractions of the elastic tube 20. Numerous other techniques for rendering the conductive loop 18 extensible, and for securing the conductive loop to the elastic tubular member 20, are disclosed in commonly assigned U.S. Pat. No. 4,308,872, the contents of which are hereby incorporated herein by reference in their entirety.

Changes in the volume of the neck underlying the transducers 12a, 12b, or in the cross-sectional area, circumference or partial circumference thereof, cause the tubes 20a, 20b, and hence the conductive loops 18a, 18b supported thereon, to expand and contract. This, in turn, results in changes in the self-inductance of the loops. If, for example, each loop 18a, 18b is incorporated as the inductance element of an LC oscillator circuit, changes in the self-inductance of the loops will be reflected as changes in the output frequencies of the respective LC oscillators in which they are incorporated. These frequency changes may then be converted to corresponding voltage signals for display on one or more suitable output devices.

Apparatus suitable for converting inductance changes of the loops 18a, 18b to corresponding voltage signals is commercially available. The presently preferred apparatus comprises a Model 100D distributed by Nims, Inc., Miami Beach, Fla., which is adapted for direct connection to the free ends of the conductive loops 18. The Model 100D incorporates the LC oscillator circuitry described above, and further includes gain controls for regulating the amplitude of the resulting voltage output signals.

It will be apparent to those of ordinary skill in the art that neck volume changes detected by the transducers 12a, 12b will result not only from changes in the blood volume of the neck, but also from changes due to breathing. Since only the signal resulting from blood volume changes is of interest, signal changes caused by breathing must be removed. Presently, two techniques are employed for removing the breathing component of the signal, namely, ensemble averaging and high pass filtering. Though the tracings shown in FIGS. 2-4 were made using ensemble averaging, high pass filtering is actually preferred, as the accuracy of ensemble averaging is dependent on the regularity of the heartbeat and, consequently, irregular heartbeats skew the results.

Because changes in neck volume caused by blood volume changes occur much more rapidly than those due to breathing, by filtering the output signals from the Model 100D with a high pass digital filter having a cutoff frequency of, for example, 0.35 Hz, the respiration component of the output signals is filtered out, leaving the cardiac component. As more fully described below, a suitable digital high pass filter can be programmed with a digital computer. Similarly, "noise" can be removed by employing a low pass analog filter to remove frequencies above, for example, 15 Hz, and a low pass filter suitable for this purpose is incorporated in the Model 100D.

Ensemble averaging may be carried out using, as a trigger, the R wave of the EKG or the upstroke of a systemic arterial pulse obtained non-invasively or invasively. Preferably, ensemble averaging is carried out with a computer using, for example, 50-100 heart beats.

Yet a third possible technique for removing the respiration signal comprises matching the lower frequency respiration component of the raw signal, using a conventional curve fitting equation, with a least squares third order polynomial fit over sequential cycles, each of which comprises two cardiac beats. If this curve fit is then subtracted from the raw signal, the higher frequency cardiac signal remains. Discontinuities resulting from the curve fitting technique may be eliminated by employing conventional smoothing techniques to adjacent curve fits in a manner well known to those of ordinary skill in the art. Again, "noise" may be eliminated by filtering out high frequencies.

Of course, if recordings are taken during breath holding, the various techniques described above for removing the respiration component become unnecessary. However, it is anticipated that in most applications breath holding will not be employed.

Figure 2:
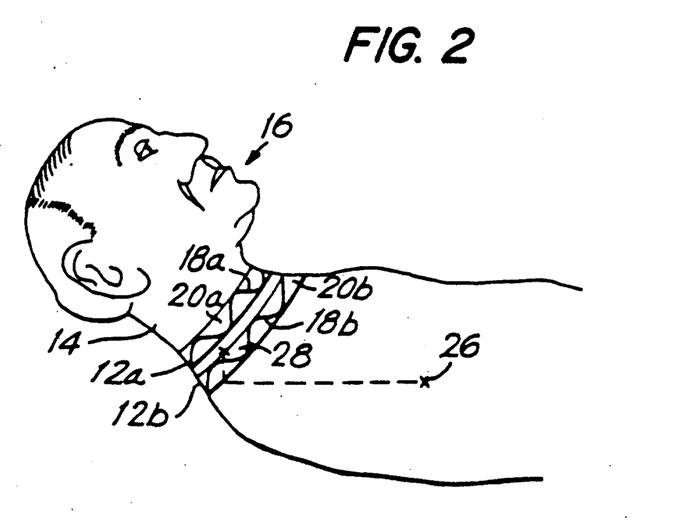
FIG. 2 is a diagrammatic representation similar to FIG. 1, but showing the subject in a more supine position.
Figure 3:
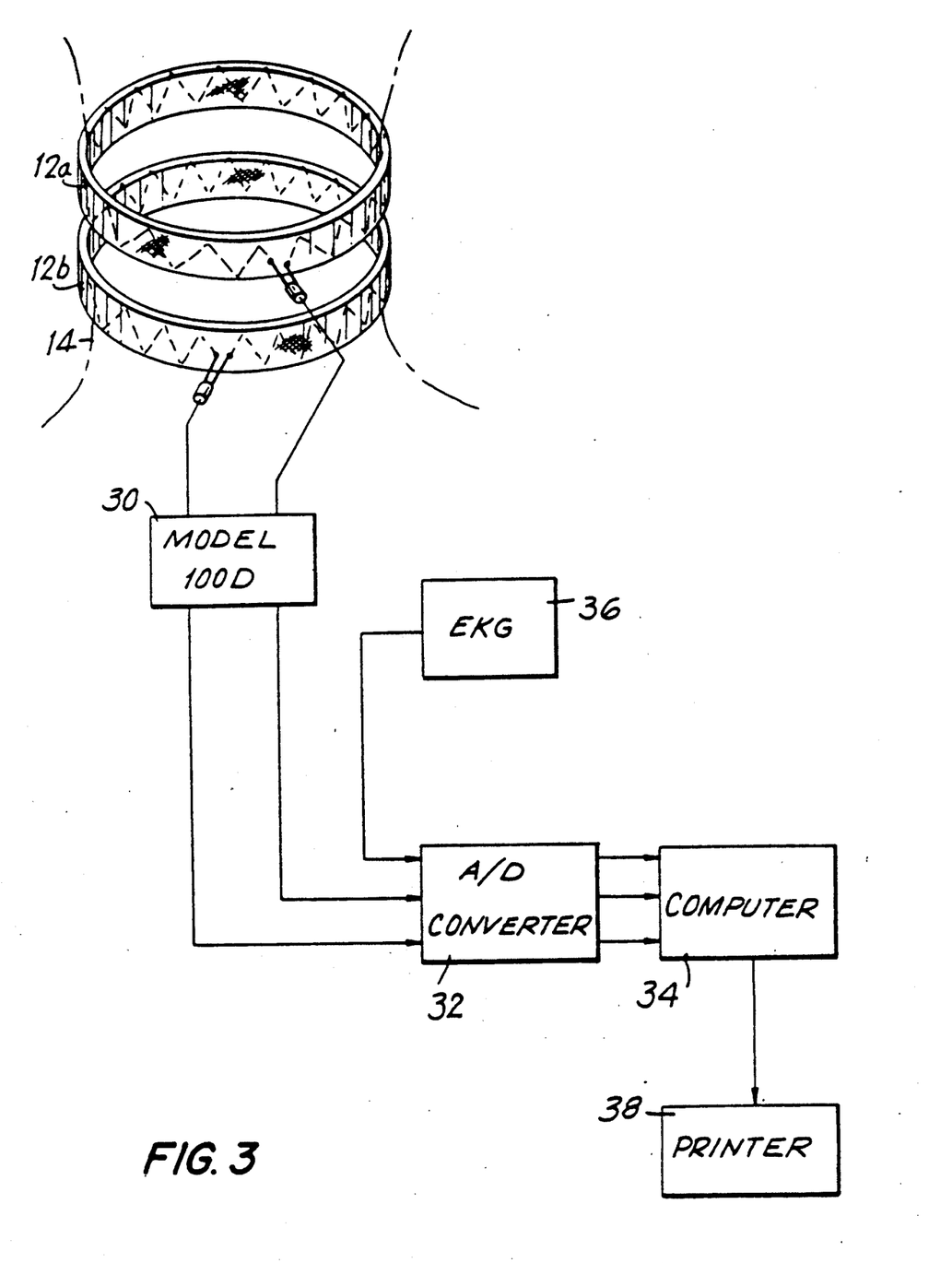
FIG. 3 is a diagrammatic representation of part an apparatus for practicing the method of the invention.

Referring now to FIGS. 1-3, the derivation and significance of the tracings of FIGS. 4-6 will now be described. As shown in FIG. 1 the transducers 12a, 12b are disposed in spaced parallel relation about the neck 14 with the transducer 12b placed at the base of the neck just above the clavicles, and the transducer 12a placed immediately cephalad to it. As shown in FIG. 3, with the transducers 12a, 12b thus placed, the free ends of the conducting loops 18a, 18b are connected to the Model 100D, designated as 30 in FIG. 3, the output of which is connected, via an analog to digital convertor 32, to a computer, such as the AST Premium/386 manufactured by AST Research, Inc. of Calif., U.S.A., the computer being designated at 34 in FIG. 3. As shown, an EKG signal from an EKG apparatus 36 is also applied to the analog to digital converter 32.

Figure 5:
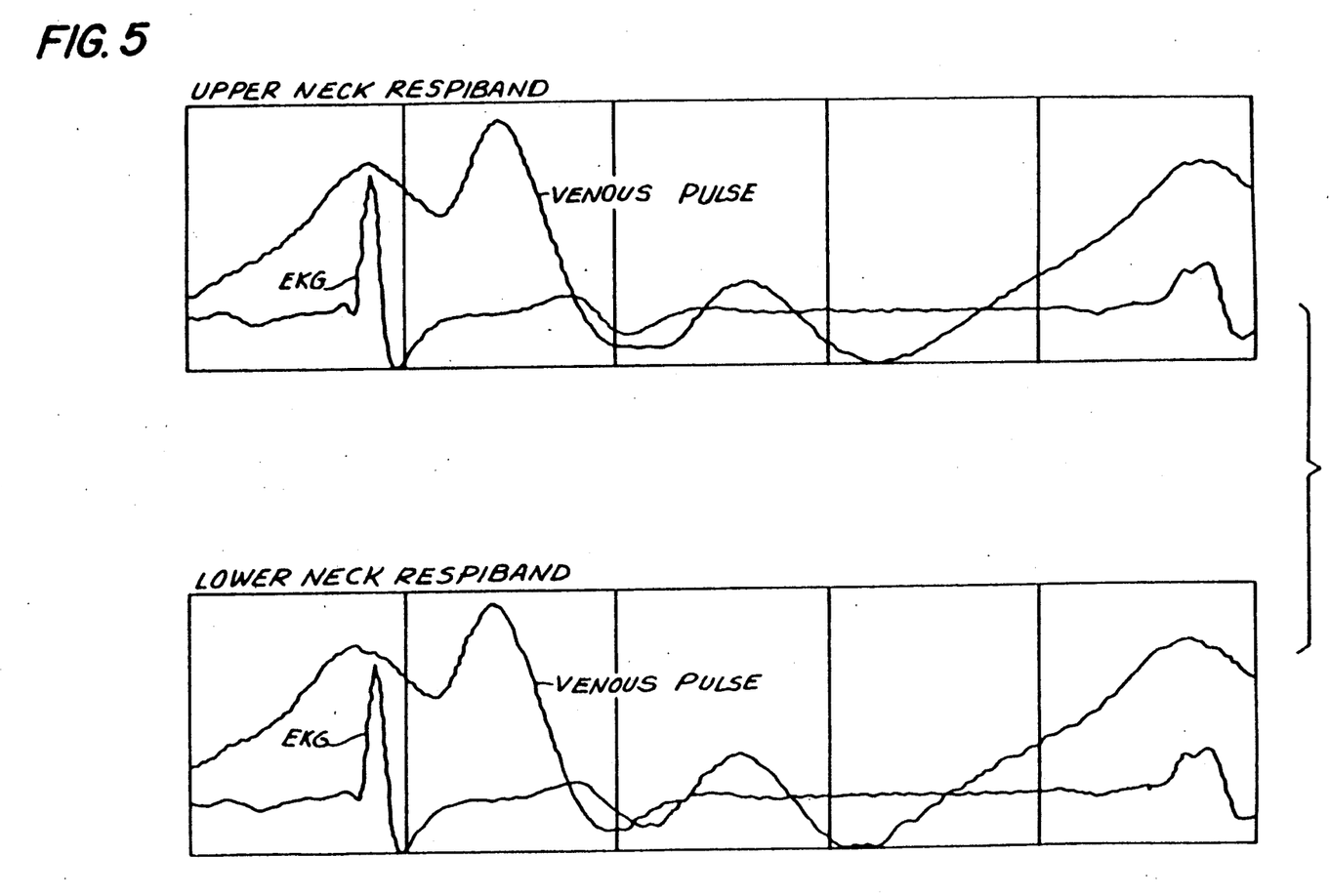
FIG. 5 is a graphic recording of waveforms from the upper and lower transducers in FIG. 2, and also showing the EKG.
Figure 6:
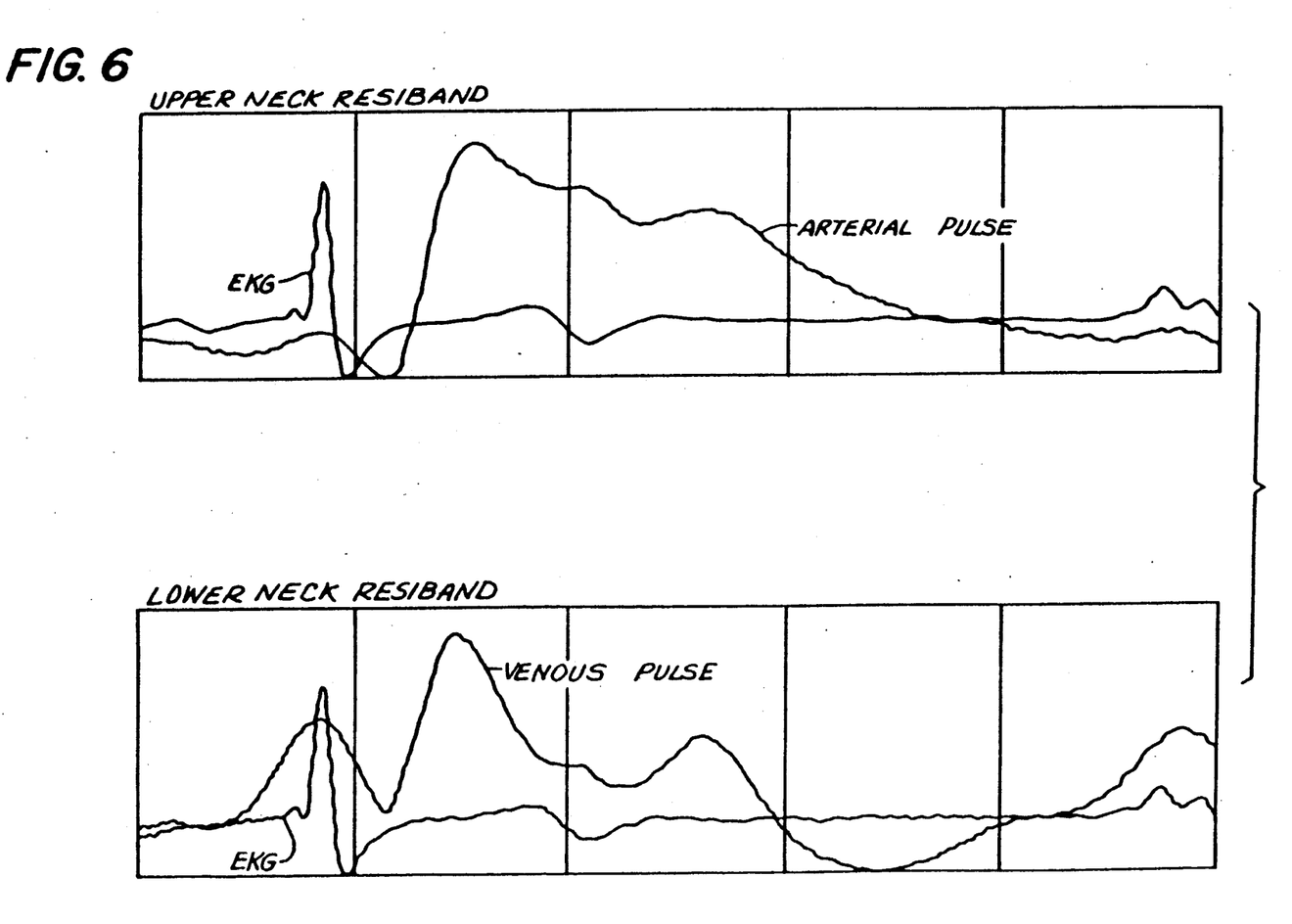
FIG. 6 is another graphic recording of waveforms from the upper and lower transducers in FIG. 1, again also showing the EKG.
Figure 7:
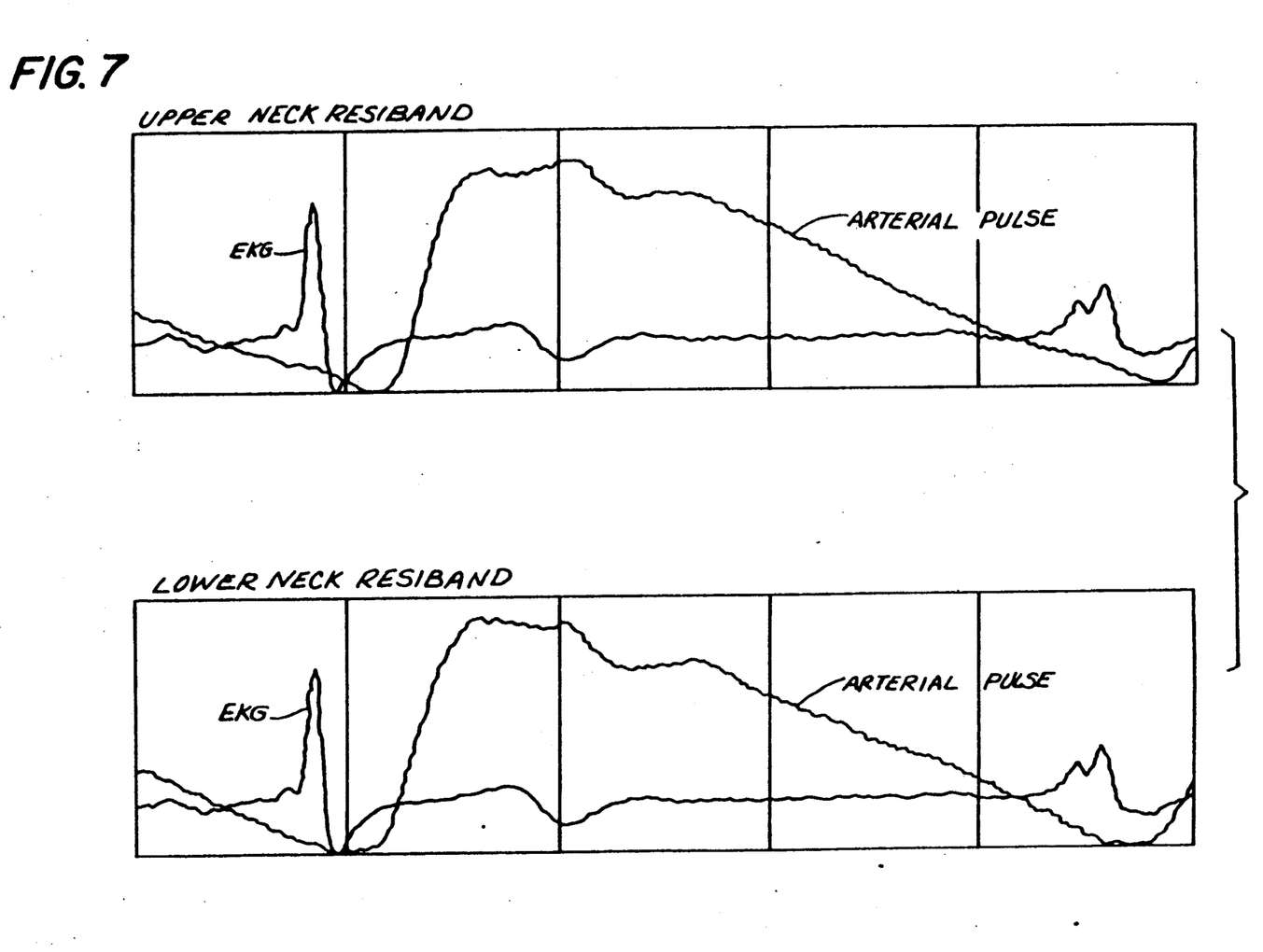
FIG. 7 is yet another graphic according of waveforms from the upper and lower transducers, also showing the EKG.

The computer 34 is programmed to subtract the respiration component from each digitized transducer signal by ensemble averaging the transducer signals using the R wave of the EKG as a trigger, with the resulting cardiac signals printed out on a laser printer 38, such as the Hewlett-Packard LaserJet Series II manufactured by Hewlett-Packard Company of Calif., U.S.A., typical recordings being shown in FIGS. 5-7, which also display the EKG signal. Programming the computer for ensemble averaging the transducer signals is well within the ability of the person of ordinary skill in the art, and accordingly a further description is deemed unnecessary.

If, in lieu of ensemble averaging, the respiration component is removed by high pass filtering, the EKG apparatus 36 may be eliminated, and the computer 34 programmed to carry out the high pass filtering. Again, programming the AFT386 for such high pass filtering is well within the capabilities of the person of ordinary skill in the art.

The recording of FIG. 5 was taken with the subject 16 in a substantially supine position. As shown, when the subject 16 is so positioned, the recordings from both transducers 12a, 12b depict jugular venous waveforms. As the upper portion of the subject's body is elevated as by means of a tilt table or hospital bed, to the semi-recumbent posture, a transition point is reached at which the signal from the upper transducer 12a depicts a mixed venous-arterial or arterial waveform, with the lower transducer 12b still depicting a jugular venous waveform. This point is depicted in FIG. 6, wherein it can be seen that the signal from the upper transducer 12a has the configuration of an arterial waveform, and the signal from lower transducer 12b still has the configuration of a jugular venous waveform.

In accordance with the present invention, once this transition point is reached, the vertical distance (d) in centimeters from the phlebostatic axis 26 to a point 28 on the upper border of the lower transducer 12a midway in the anterior-posterior plane of the neck provides a good approximation of CVP in cmH$_2$O. In this regard, while the upper border of the transducer midway in the anterior-posterior plane, which corresponds to the point designated at 28 in FIG. 1, has been selected for this measurement, this is not critical, and other points on the transducer will also suffice, as the transducer is of limited height and the result an approximate, rather than exact, measure of CVP. It should be understood that this comment applies to all the embodiments discussed in this application.

Figure 4:
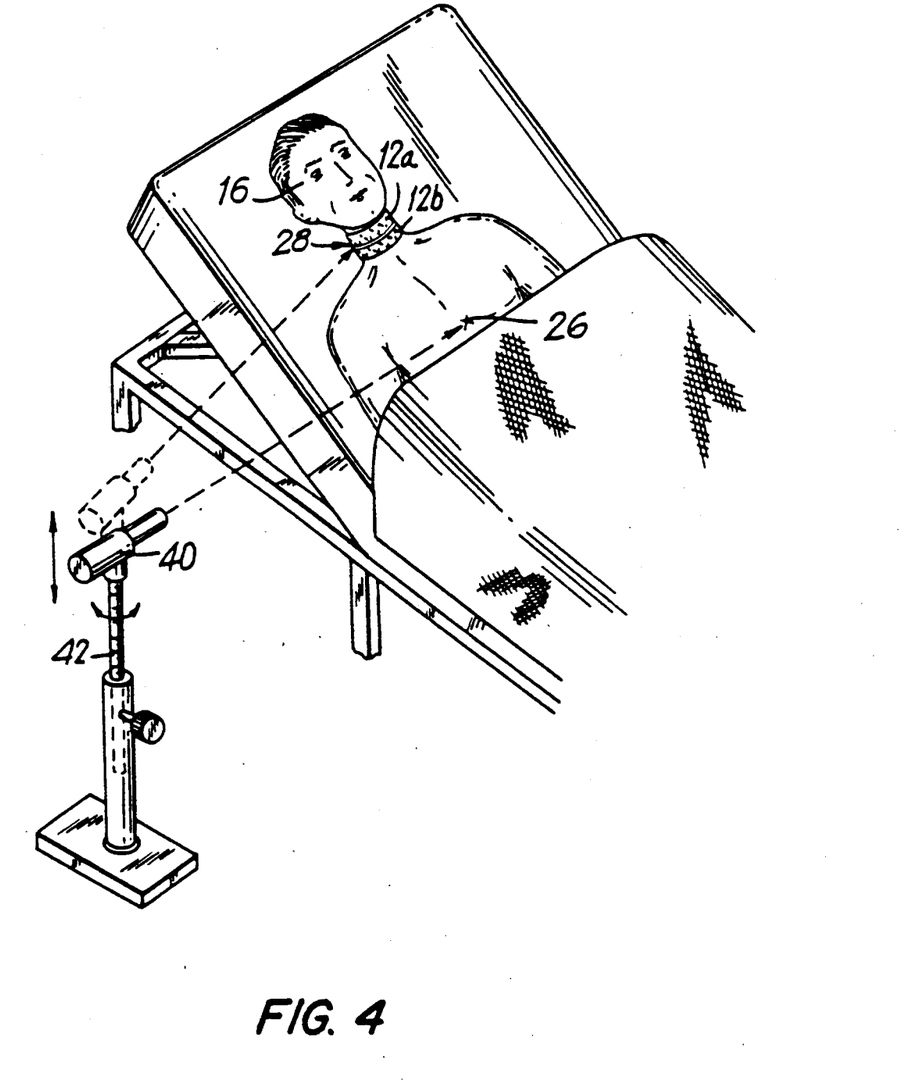
FIG. 4 is a perspective view of another part of the apparatus for practicing the method of the invention.

While those of ordinary skill in the art who read this description will recognize that there are several ways to measure the vertical distance (d) from the phlebostatic axis 26 to the point 28, as diagrammatically illustrated in FIG. 4, the distance (d) is preferably measured using a laser light source 40 disposed on a vertical micrometer 42 calibrated in centimeters. The laser 40 is first visually sighted on the phlebostatic axis 26, and a first micrometer reading noted. Then, the laser is swiveled and raised (dotted lines in FIG. 4) until it is focused on the point 28. Assuming the waveform from the upper and lower transducers 12a and 12b are as depicted in FIG. 6, the vertical distance (d) in centimeters from the first micrometer reading to the second provides a good approximation of CVP in cmH$_2$O. If desired, a potentiometer or other suitable electrical device may be connected to the micrometer for providing, as in response to depression of a manual switch, a signal indicative of the micrometer reading, whereupon the two above-mentioned readings can then be processed, as by a computer, for calculating the distance (d) as the difference between the two readings. As the manner of fitting the micrometer with a potentiometer and for processing the signals generated thereby is well within the capabilities of the person of ordinary skill in the art, a further description thereof is deemed unnecessary.

FIG. 7 depicts waveform recordings from the transducers 12a, 12b with the upper body portion of the subject 16 tilted upward beyond the semi-recumbent position of FIG. 1. As shown in FIG. 7, the waveforms from the transducers 12a, 12b both depict arterial waveforms, indicating that the subject 16 must be tilted downward to achieve the waveforms depicted in FIG. 6 wherein the distance (d) in centimeters from the phlebostatic axis 26 to the point 28 provides a good approximation of CVP in cmH$_2$O.

Figure 8:
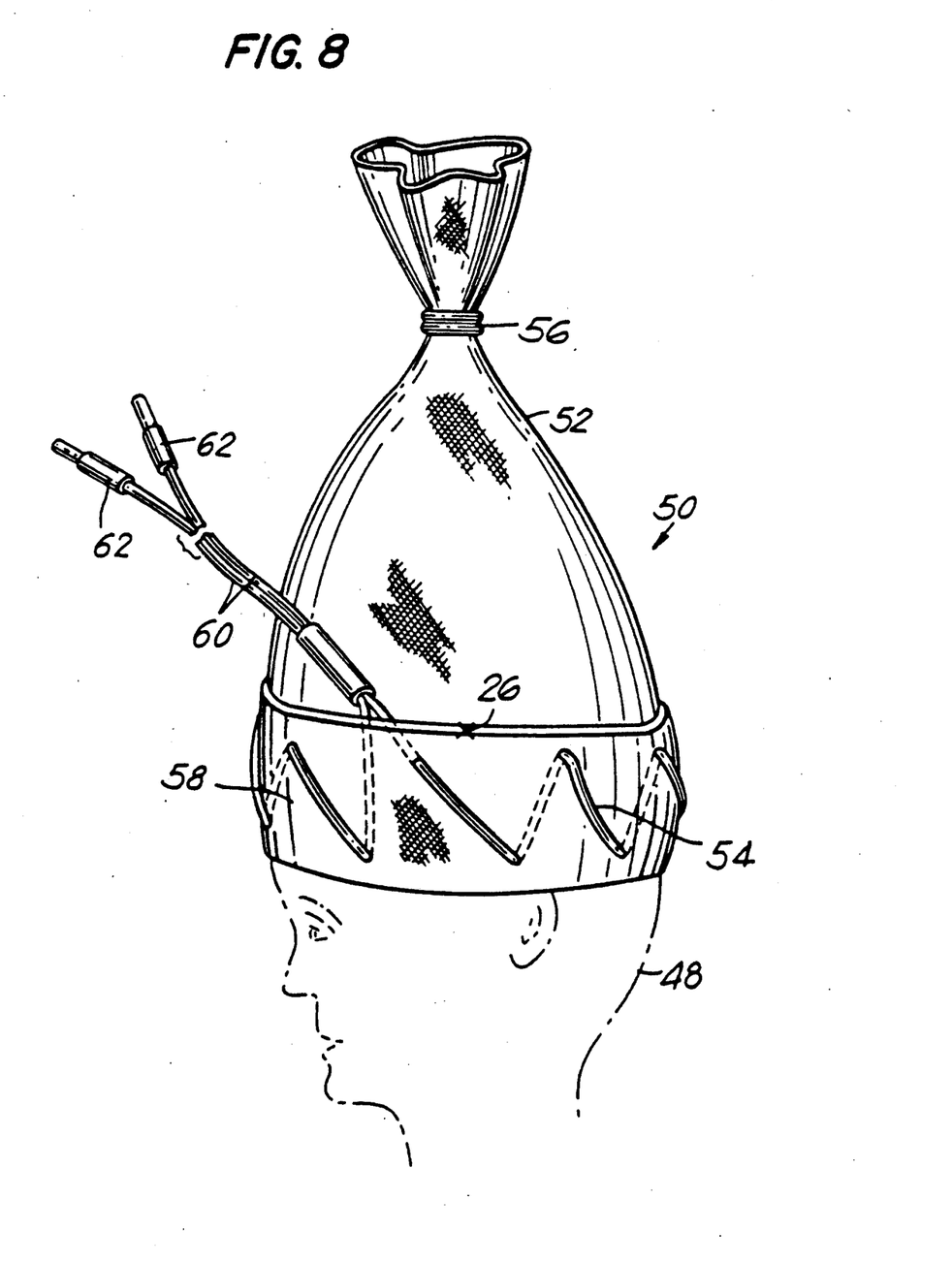
FIG. 8 is perspective view of another transducer suitable, inter alia, for practicing the method of the invention.

Referring now to FIG. 8, the method of the present invention may be used to monitor CVP in infants up to the age of about 18 months by placing a transducer about the head, rather than the neck. In accordance with another aspect of the invention, FIG. 8 shows a transducer 50 especially adapted for this purpose.

As shown, the transducer 50 comprises a cap 52 having a conductive loop 54 threaded therein. The cap 52 basically comprises a conventional stocking cap of the type placed on the head of a newborn for keeping the newborn warm. The preferred cap comprises a tube of stretchable material closed at one end as by a rubber band 56. The other end of the tube is folded back on itself for defining a hem 58, and the conductive loop 54 is threaded through the hem 58 with the free ends 60 of the loop 54 extending away from the cap 52 and terminating in connectors 62 suitable for connection to a Nims Model 100D.

In use, the cap 52 is placed on the infant's head with the conductive loop 54 encircling a cylinder defined, in part, by the infant's forehead. The stretchability of the stocking cap 52 and the up-and-down threading of the conductive loop 54 in the hem 58 accommodate the expansion and contraction of the conductive loop 54 as the underlying cranial volume varies. The cranial volume, in turn, varies with changes in the cranial pressure and also with respiration. Changes in the shape of the loop 54 result in changes in the inductance thereof, these changes being translated to an analog voltage signal by the Nims Model 100D in the manner described above in connection with the description of FIGS. 1–7. In studies done to date, the output of the Model 100D has been applied to a digital high pass filter having a cut off frequency of about 0.8 Hz for filtering out the respiration component of the signal, with the resulting cardiac component displayed in an analog format on an oscilloscope (not shown). As noted above, a suitable digital high pass filter can be programmed in the AST Premium/386.

Still referring to FIG. 8 when the infant 48 is supine, a venous waveform is depicted on the oscilloscope. If the upper body portion of the infant is then raised, as by tilting an incubator in which the infant is disposed, a point is reached at which the signal switches over to an arterial or mixed venous-arterial waveform. At that point, the vertical distance (d) from the phlebostatic axis to the point 26 on the transducer 50 provides a good approximation of CVP in cmH$_2$O. This distance can be measured using, for example, the apparatus of FIG. 4.

From the foregoing description of how the method may be practiced in infants, it should now be apparent that the method of the invention may be practiced using a single transducer, as contrasted with the dual transducers described above in connection with FIGS. 1–7, though there is an advantage to utilizing dual transducers. In particular, by employing dual transducers, trends in CVP may be monitored. For example, and referring again to FIGS. 1–7, as long as the subject 16 assumes a posture in which the waveforms from the upper and lower transducers 12a, 12b are as depicted in FIG. 6, the vertical distance (d) provides a good approximation of CVP. Should CVP increase, the waveforms from the transducers 12a, 12b will assume the configuration shown in FIG. 5, i.e. the waveform from the upper transducer 12a will change to a venous configuration. This will indicate that CVP has increased, providing valuable CVP trend information to health care personnel.

In the same manner, if the waveforms from the transducers 12a, 12b are as depicted in FIG. 6 and CVP drops, the waveforms will assume the configuration of FIG. 7, i.e. the signal from the lower transducer 12b will depict an arterial or mixed venous-arterial waveform, again providing valuable CVP trend information to health care personnel. In either case, if desired, actual CVP can be determined by raising (if CVP has increased) or lowering (if CVP has decreased) the upper body portion of the subject 16 until the waveforms from the transducers 12a, 12b again assume the configuration in FIG. 6, i.e. the upper transducer 12a depicts an arterial or mixed venous-arterial configuration and the lower transducer 12b depicts a venous configuration, whereupon the new CVP can be determined using the apparatus of FIG. 4 in the manner described above.

By employing suitable signal discriminating circuitry, the design of which is within the capabilities of the person of ordinary skill in the art, a buzzer or other alarm, aural or visual, may be activated if CVP decreases (as indicated by the waveform of the lower transducer 12b changing from a venous configuration to an arterial or mixed venous-arterial configuration) or increases (as indicated by the waveform of the upper transducer 12a changing from an arterial or mixed venous-arterial configuration to a venous configuration). Since, as described earlier, changes in CVP serve an important diagnostic function the ability to monitor trends in CVP in the manner described herein is significant.

Though not as useful as the trend information available from two transducers, limited trend information can be obtained using a single transducer. For example, referring again to FIG. 8, if the transducer initially depicts a waveform having an arterial or mixed venous-arterial configuration, a change in the waveform to a venous configuration will indicate a rise in CVP. Conversely, if the transducer initially depicts a venous configuration, a change to an arterial or mixed venous-arterial configuration will indicate a drop in CVP. By employing signal discriminating circuitry to detect changes in the transducer waveform from a venous configuration to an arterial or mixed venous-arterial configuration or vice versa, a buzzer or other alarm, aural or visual, may be activated to advise health care personnel of a change in CVP.

Proper placement of a single transducer for monitoring in this fashion is readily accomplished. Initially, the position of the subject's upper body is adjusted until the point is detected at which the transducer waveform transitions between a venous configuration and an arterial or mixed venous-arterial configuration. Alternatively, this point may be determined by adjusting the position of the transducer on the subject, or by a combination of repositioning the subject's upper body and adjusting the position of the transducer, though if this technique is practiced with the transducer 50 of FIG. 8, adjusting the position of the infant may be the only viable option. In either event, at that point, the vertical distance (d) in centimeters from the phlebostatic axis to the upper border of the transducer midway in the anterior-posterior plane approximates CVP in $cmH_2O$.

Once the transition point is located, and assuming it is desired to monitor increases in CVP, the position of the transducer and/or the position of the upper body of the subject is raised until an arterial or mixed venous-arterial configuration is achieved Again, for the case of the transducer of FIG. 8, adjusting the position of the subject may prove the only viable option In any event, after adjustment to achieve the arterial or mixed venous-arterial configuration, a change to the venous configuration will indicate a rise in CVP. Conversely, if after the transition point is located the transducer and/or subject position are lowered until the waveform depicts a venous configuration, declines in CVP will be indicated by a change in the waveform from the venous configuration to the arterial or mixed venous-arterial configuration.

As noted above, the transducer depicted in FIG. 8 is novel per se, and has applications beyond the practice of the method of the present invention. For example, the transducer 50 of FIG. 8 may be utilized to monitor intrapleural pressure and/or in conjunction with, for example, a nasal cannula, to differentiate between central and obstructive apneas and hypoapneas, all in the manner described in commonly assigned U.S. Pat. No. 4,648,407, the entire contents of which are hereby incorporated herein by reference, the transducer 50 being substituted for the surface inductive plethysmograph transducer described in said patent. Also, if desired, the signal from the transducer 50 may be split into two components, one of which is high pass filtered for extracting the cardiac component and the other of which is low pass filtered for extracting the respiration component. In this way, the single transducer 50 may be used to monitor both CVP and intrapleural pressure or, if the subject's head is raised sufficiently relative to the phlebostatic axis, the arterial pulse and intrapleural pressure. It should be noted, however, that because the movements detected by the transducer 50 are accommodated by the fontanels and sutures, which disappear as the cranial bones fuse, the transducer 50 is only effective in newborns up to a maximum age of about eighteen months.

Figure 9:
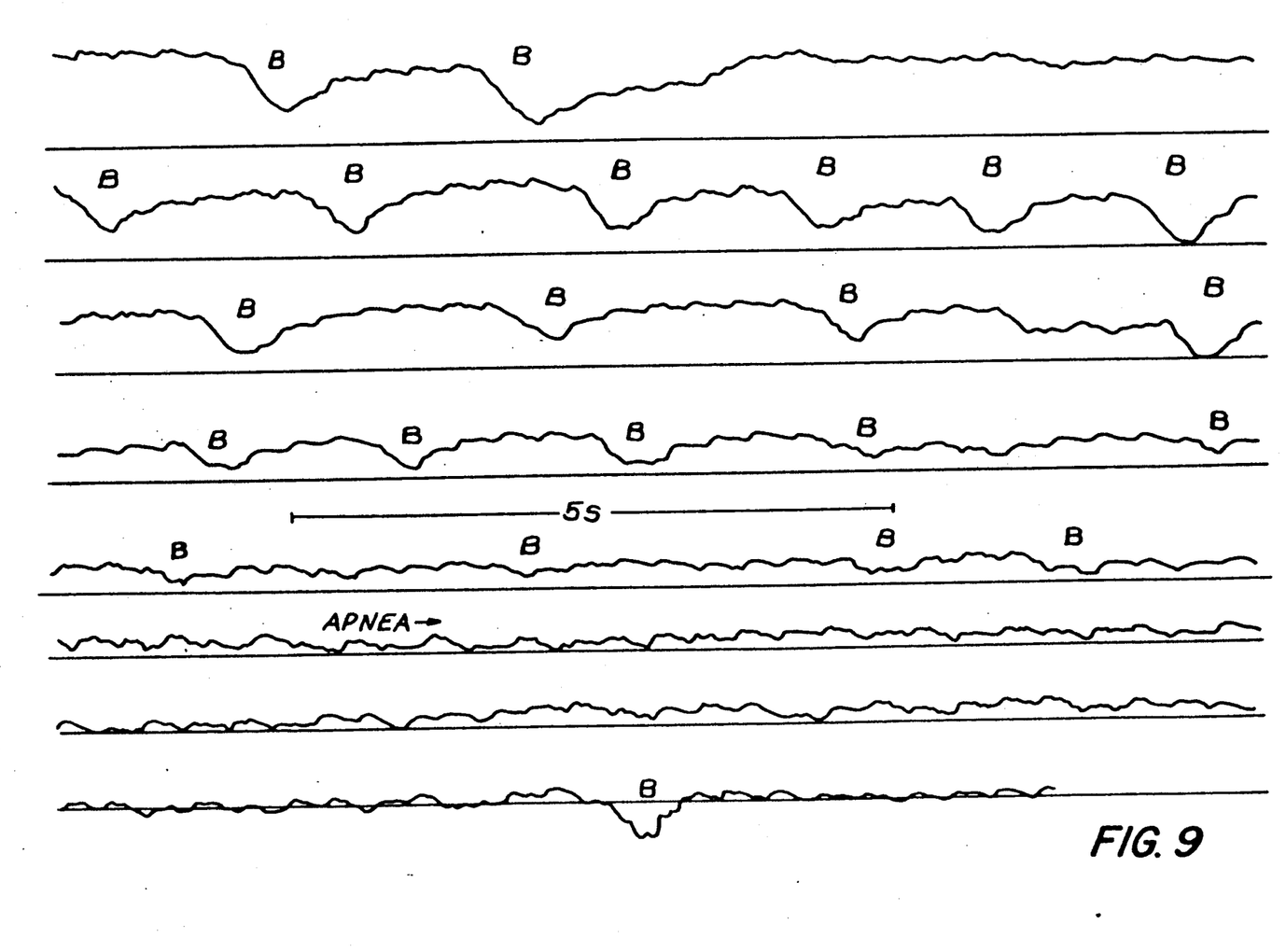
FIG. 9 is a graphic recording of a waveform from the transducer of FIG. 8.

FIG. 9 shows a real time recording made with the transducer 50 disposed about the head of an infant, the recording being separated into eight separate panels in FIG. 9 for placement on a single sheet, with time extending from the upper left to the lower right. For purposes of illustration, the signal shown is not processed for removing either the respiration or cardiac components. The notation "5s" on the fifth panel indicates that the demarcated section of the recording represents five seconds in real time. The lower frequency waveform in the upper four panels is the respiration signal, with each "B" indicating a new breath. The higher frequency oscillations on the respiration signal depict vascular function. The absence of breaths in the lower four panels indicates an apnea.

While I have herein shown and described the preferred embodiments of the present invention and suggested certain modifications thereto, those of ordinary skill in the art will recognize that still further changes and modifications may be made therein without departing from the spirit and scope of the invention. Accordingly, the above description should be construed as illustrative and not in a limiting sense, the scope of the invention being defined by the following claims.

I claim:

1. A transducer for monitoring cardiopulmonary events in a subject comprising:
    a cap formed by a tube of stretchable material closed at one end, the other end of said tube being dimensioned for a close fit about the head of the subject;
    a conductor comprising a conductive loop;
    means for securing said conductive loop in a flexible configuration about said other end of said stretchable tube for fitting said conductive loop about the head of said subject and for expansion and contraction of said conductive loop with said subject's head in response to said cardiopulmonary events with changes in the configuration of the loop as a result of said expansion and contraction resulting in corresponding changes in the inductance of said loop; and
    means for insulating said conductor for preventing contact between said subject and said conductor.

2. The transducer of claim 1, wherein said other end of said tube is folded back on itself to define a hem, and wherein said means for securing said conductive loop comprises means for threading said conductive loop in a flexible configuration to said hem.

3. The transducer of claim 2, wherein said conductive loop comprising said conductor is threaded in a flexible configuration which extends in an up-and-down fashion about a width of said hem for accommodating expansion and contraction of said conductive loop.

4. The transducer of claim 1, wherein said tube comprises a stretchable cloth material.

5. The transducer of claim 1, further comprising an LC oscillator, and wherein the inductance of said conductive loop comprising said conductor changes in conjunction with changes in the configuration of the loop as a result of expansion and contraction thereof, and wherein said conductor is incorporated as an inductance element in said oscillator such that changes in the inductance of the conductive loop comprising the conductor effect corresponding changes in the variable frequency of the oscillator.

6. The transducer of claim 5, further comprising means for converting the variable frequency output from the oscillator to a corresponding variable voltage signal.

* * * * *